(12) United States Patent
Niazi

(10) Patent No.: US 9,587,214 B2
(45) Date of Patent: Mar. 7, 2017

(54) BIOREACTOR EXHAUST

(71) Applicant: Sarfaraz K. Niazi, Deerfield, IL (US)

(72) Inventor: Sarfaraz K. Niazi, Deerfield, IL (US)

(73) Assignee: Adello Biologics, LLC, Chicago, IL (US)

( * ) Notice: Subject to any disclaimer, the term of this patent is extended or adjusted under 35 U.S.C. 154(b) by 168 days.

(21) Appl. No.: 14/685,250

(22) Filed: Apr. 13, 2015

(65) Prior Publication Data

US 2015/0210974 A1 Jul. 30, 2015

Related U.S. Application Data

(63) Continuation of application No. 13/098,462, filed on May 1, 2011, now Pat. No. 9,005,959.

(51) Int. Cl.
| | |
|---|---|
| *A01N 1/00* | (2006.01) |
| *A01N 1/02* | (2006.01) |
| *C12M 1/00* | (2006.01) |
| *C12M 1/34* | (2006.01) |

(52) U.S. Cl.
CPC ............ *C12M 29/20* (2013.01); *C12M 23/26* (2013.01); *C12M 23/28* (2013.01); *C12M 41/40* (2013.01); *Y10T 137/0379* (2015.04); *Y10T 137/6416* (2015.04)

(58) Field of Classification Search
CPC ........ C12M 7/02; C12M 35/04; C12M 21/04; C12M 23/14; C12M 29/10; C05F 17/0205; C05F 17/0258; C05F 17/027; C05F 17/02; C05F 17/0063
See application file for complete search history.

(56) References Cited

U.S. PATENT DOCUMENTS

| | | | |
|---|---|---|---|
| 2009/0263296 A1* | 10/2009 | Taques | B01D 46/30 422/177 |
| 2011/0259442 A1* | 10/2011 | McBride | H02J 15/006 137/334 |

\* cited by examiner

*Primary Examiner* — Michael Hobbs
(74) *Attorney, Agent, or Firm* — Adello Biologics, LLC; Sarfaraz K. Niazi; Cheryl Liljestrand

(57) ABSTRACT

An exhaust system suitable for high volume exhaust from flexible disposable bags is described that prevents nutrient media volume loss and prevents cross-contamination without using any filters. The invention described here allows the use of disposable two-dimensional bioreactors for the cultivation of bacterial and other organisms and cells require high aeration.

10 Claims, 3 Drawing Sheets

BIOREACTOR EXHAUST

CROSS REFERENCE TO RELATED APPLICATION

This application is a continuation of U.S. patent application Ser. No. 13/098,462, now U.S. Pat. No. 9,005,959, entitled "Bioreactor Exhaust" filed on May 1, 2011, the contents of which are incorporated herein by reference in its entirety.

FIELD OF THE INVENTION

The instant invention generally concerns the design of disposable flexible bioreactors, more particularly to the use of disposable bioreactors in the cultivation of organisms requiring high rate of gasification.

BACKGROUND OF THE INVENTION

Flexile disposable bioreactors are fast becoming the most desirable means of manufacturing biological products. However, the application of these devices has been severely restricted because of the inability to provide high aeration and exhaust needed to grow bacteria and other organisms and cells and as a result, the applications of the two dimensional flexible bioreactors has remained restricted to cell culture that does not need high degree of gasification. Even when disposable flexible bioreactors are used for cell culture, their sizes have been limited again by the quantity of gas that can be provided inside the bioreactor and more important how fast the gas can be removed from the bioreactors.

The reason why the two dimensional flexible bag technology has not found its deserved place in the manufacturing systems is that much of the thinking that went into a creating three-dimensional technology was carried over to the two-dimensional world. A one less dimension meant a one giant change in thinking that never came. There is a need to take a fresh look at the core technology and revamp it to make the flexible bag more useful in the manufacturing of biological drugs. In the words of one of the most famous poets of Asia, Mirza Asadullah Khan Ghalib as translated by the inventor:

"A monotheist we are, it is in our resolve to reject traditions. When dogmas are decimated, they become ingredients of a new belief."

Growing bacteria requires extensive aeration and thus very large exhaust outlets and while this would not be an issue for the hard-walled bioreactors. Flexible bioreactors have the problem of changes in the pressure as bags expand and contract carrying the risk of drawing room air inside the bag and also of exhausting liquid particles carrying biological culture that will contaminate the room. There is also the problem of any liquid particles laden with live organisms leaving the bioreactor to the environment. To overcome these problems, the exhaust port of disposable bioreactors in the current art is provided with a filter that prevents both incidences. This works well as long as the volume of gas exhausted is small but when hundreds of liters of air will be exhausted out, this will require extremely large filters and even then, building a backpressure will be inevitable.

It is important to know that while cell culture growth in the flexible bags is promoted by exchange of gases across the surface while the bags build a certain pressure, growth of bacterial cultures requires intense aeration that can not be accomplished by surface aeration and thus pressurization is useless and can even be damaging to the bioreactor as large volumes are passed through the bag and even small changes in the resistance to flow would add significant pressurization of the flexible bags.

Large exhausting of gases also carries the risk of loosing moisture from the bags resulting in significant volume changes.

There is no prior art in the field of bioreactor exhaust systems suitable for disposable flexible bags when used to grow bacteria or other cells and organisms require large volume of exhausts.

SUMMARY OF THE INVENTION

Flexible disposable bags are contraindicated in the current art to grow bacteria because of the inability of these bags to control the aeration of nutrient media necessary for the growth of bacteria and other similar organisms and cells that require large aeration. Three problems are identified in exhausting the gases out of the flexible disposable bioreactors: pressure fluctuation in the exhaust port that might draw air from the room, back up pressure if any resistance is provided to the flow of gases such as adding a filter, and loss of water due to convective effects. Not being able to resolve these problems, no manufacturer of bioreactor equipment sells a large-scale disposable flexible bioreactor for bacterial fermentation. However, the cost and safety benefits of using disposable flexible bags are enormous and there should be means developed to over come these difficulties in the use of disposable flexible bioreactors.

The instant invention teaches a bioreactor exhaust assembly design that is suitable for any size of nutrient media in a flexible bioreactor bag as it can exhaust any volume of gas using a design that does not require use of a filter, yet reduces loss of moisture and prevents cross contamination.

Additionally important, the instant invention provides a much cheaper solution to manufacture of biological drugs using biological culture that requires intensive aeration.

The instant invention comprises returning back the condensation of the gas effluent coming out of a bioreactor, it is expected that more than 99% of exhausted moisture is captured at this stage. Keeping the exhaust tube cold and adjusting the size of the tube to allow sufficient dwell time in the cold tube accomplishes this; both of these variables easily worked out by measuring moisture coming out exhaust tube. Additionally, the instant invention comprises condensation of any remaining moisture in the cold condenser where the exhaust air directly contacts a metallic surface that is more likely to produce a quick precipitation preventing exhaust of any liquid particles laden with biological culture to the clean environment. The condensed moisture is not allowed to contaminate the room by retaining it in the condenser box. The condenser box has monitors for pressure and when the pressure rises above a certain level (e.g., at least 0.05 inch water gauge), an exhaust valve opens and discharges the gases in the atmosphere. A positive pressure is always maintained inside the condenser box to assure that no air enters the exhaust systems from the room.

The instant invention can be used with any type of bioreactor and any size, both hard-walled and flexible wall type and can manage any volume of gas flow as the dimensions of the components of the bioreactor exhaust disclosed here can be varied to suit the needs of the bioreactor exhaust anticipated.

Also disclosed are the methods of using the bioreactor exhaust and of manufacturing biological drugs using a bioreactor connected to the instant invention.

DETAILS OF THE INVENTION

Figure 1:
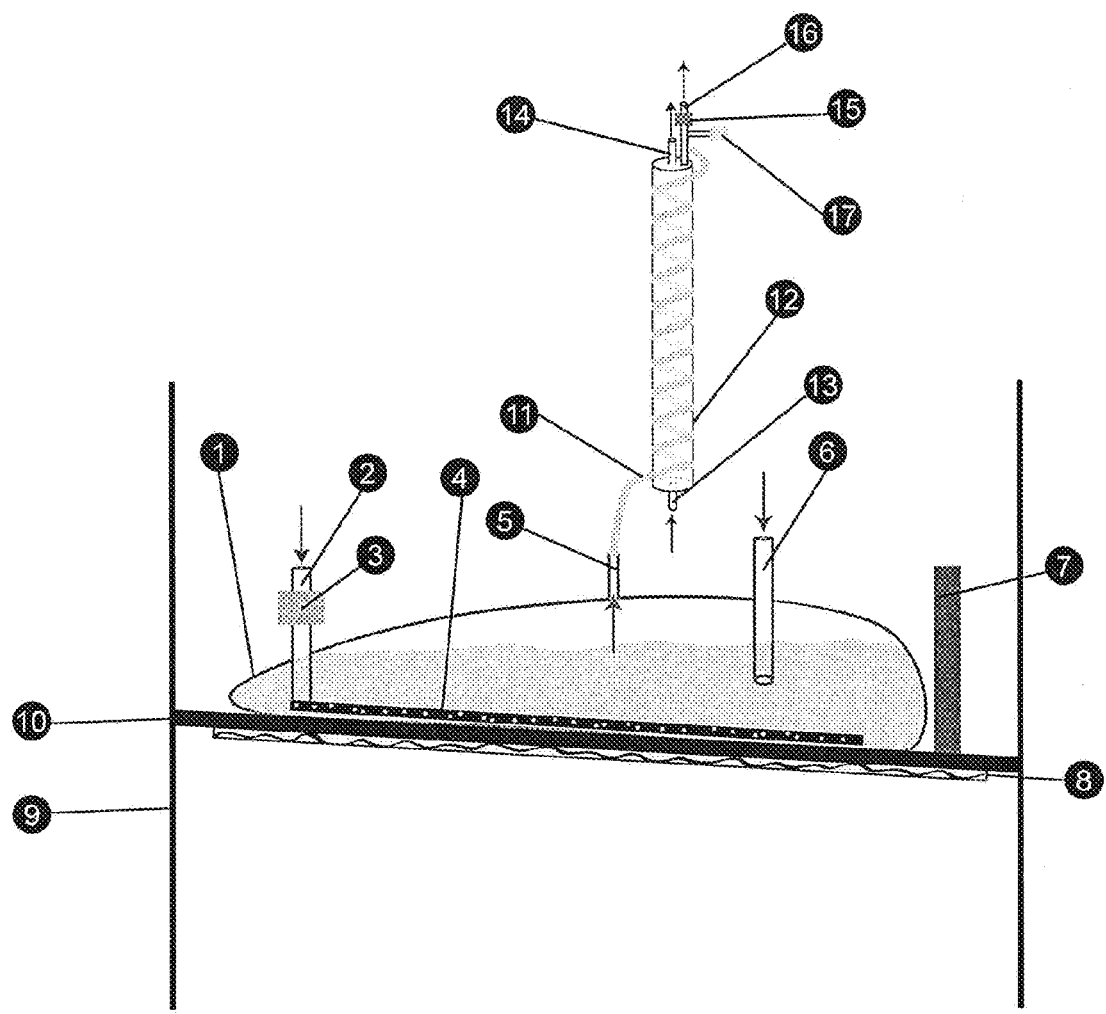
FIG. 1 is a lateral view of a bioreactor exhaust assembly with condenser and connected to a disposable bioreactor.

Flexible bioreactors in the current art cannot be used to grow bacterial culture and other such biological cultures that require high rate of aeration. To achieve an appropriate KLA value, these biological cultures must be adequately supplied with gases like oxygen. It is not uncommon to use an aeration of one volume per volume of media (vvm). While at smaller sizes, these flow rates can be easily managed using the current art, a commercial production bioreactor requiring ability to vent out 100 s to 1000 s liters of gas per minute. None of the commercially available flexible bioreactors can handle this flow rate. Even if these bioreactors were modified for the size of the exhaust port, pushing such large volume of air would develop a pressure in the bag that will bloat it beyond the rupture point. For example, the commonly used GE Cellbag has a maximum pressure resistance to 0.1 bar or about 1.5 psi. If the recommendations of the current art are employed and a filter is attached to the exhaust from a flexible bag, it will require a pressure much higher than the bag can be subjected to. For example, the GE Nylon-hydrophobic membranes (see Table 1) resist water while simultaneously venting air are suitable for venting but require high breakthrough pressure; while a pressure of 2.5 psi is needed for a 10 micron pore size membrane, it is 35 psi for 0.1 micron membrane. At these pressures, the bioreactor bag would inflate to a point of rupture at high flow rates such as 1 vvm regardless of the surface of filter made available. The polytetrafluoroethylene (PTFE) membranes are costlier and also require similar breakthrough pressures.

One method that can be used to remove any suspended liquid particles, no matter how fine they are, is to impact them in a path that would allow free flow of gas but remove suspended particles. The physics of impaction is well recognized and is demonstrated by how our lungs remove suspended particles in the air we breathe; the tortuous pathway of our alveoli, the sudden turning of the direction of air produces an impaction of particles on the surface lung alveoli due to their momentum effect; the suspended particles have a higher momentum since as they have a higher mass and would thus not easily follow the path of the air and thus impact the wall of the alveoli.

The bioreactor exhaust (that might contain biological culture), in most instances, would be at 37 C, laden with moisture and likely liquid particles, which may carry bacteria with them. If this exhaust is forced through a longer path, specially a tortuous path, the gases would soon condense once their temperature goes below the dew point and impact on the wall of the tube. The condensate formed in the tube, if it is kept upright and of sufficient diameter, would drain back into bioreactor.

The instant invention utilizes the principle of impaction to remove moisture and suspended liquid particles from the exhaust. Since the tubes attached to the bioreactor must be sterilized, the easiest and most obvious solution would be to use a flexible sterilized connector tube long enough for the exhaust to cool down. To make sure that no additional resistance to flow is offered by a kinked tube, the tube is wound upward around a cylindrical metal block. The diameter of the cylindrical metal block is such that the winding of the tube does not produce any kinks. The cylindrical metal block is kept cold to cool down the exhaust tube quickly and produce dew point conditions. To increase the contact between the exhaust tube and the metal block, grooves are created in the cylindrical metal block to embed the tube in it to maximize heat transfer to the exhaust tube.

The length of the tube and thus the height of the metal block would depend on the flow rate anticipated. Longer

TABLE 1

Performance Characteristics GE Nylon Hydrophobic Membrane

| Pore Size | 0.1 µm | 0.20 µm | 0.45 µm | 0.6 µm | 0.8 µm | 1.2 µm | 5.0 µm | 10.0 µm |
|---|---|---|---|---|---|---|---|---|
| Water Breakthrough Pressure or Alcohol Bubble Point, psi (kg/cm$^2$) | 35 (2.46) | 25 (1.76) | 15 (1.05) | 9.0 (0.63) | 6.5 (0.46) | 5.5 (0.39) | 3.0 (0.21) | 2.5 (0.18) |
| Typical Air Flow, (SCCM/cm$^2$/psi) | 44 | 85 | 200 | 320 | 500 | 580 | 1490 | 1930 |

(Source: http://www.gelifesciences.com)

Venting a bioreactor also requires that the biological culture does not leave the bioreactor and thus an obvious solution would be to attach a filter to the exhaust vent. However, as seen above, this cannot be done in flexible bags that must exhaust very large volumes of gases. The practice of using filters at the exhaust level is a carry over from the operation of hard-walled systems where the backpressure has little impact on the bioreactor and filters, regardless of their breakthrough pressure can be readily used. The same applies to those systems where a flexible bag is housed in a hard walled container transferring the pressure to the outer container. In fact, most of the current technology used in the operation of flexible disposable bags is a carryover from the technology used for hard-walled containers with all of its limitations.

tube would mean a longer dwell time and thus the volume of tube is an important parameter; generally a dwell time of about 1-2 seconds would be adequate; this means that the volume of tube can be about $\frac{1}{60}^{th}$ or $\frac{1}{30}^{th}$ of the exhaust volume per minute. For 100 liters per minute exhaust, a tube volume of 1-3 liters would suffice. These calculations are easy to make and should be worked out for the specific bioreaction process.

While testing does at a dwell time of 1-2 seconds works well, these values are only for general guidance and a suitable dwell time can be established by simple experiments such as placing a hygrometer at the end of the tube exhaust and measure the humidity and then adjusting the size of the tube to achieve a pre-determined low humidity.

To a great degree the dwell-time will be determined by the choice of material for the exhaust tube; a metallic tube would provide a much shorter dwell time than would a plastic tube since in the metallic tube it would relatively easy to maintain a dew point condition over a much larger flow rate range.

The condensate formed is returned to the bioreactor helping keep the volume of fluids in the bioreactor constant.

It is fully recognized that plastic is a poor conductor of heat and not the most desirable material to produce condensation of moisture, yet the fact that a plastic tube can readily be made a part of a bioreactor sterilized by gamma radiation, the invention allows the use of it and provides means to assure that the primary goals of the design are met by adding features to the systems that would assure that no liquid particles leave the bioreactor even if the condensation in the plastic tube is not complete.

A condenser box is provided that takes the exhaust out of exhaust tube and instantly chills is it to below the dew point by exposing the gas to a condenser coil kept at 5-8 C. The condensate formed in the condenser box is retained inside the box and discarded periodically.

The condenser box is kept at a lower level than the end of the exhaust tube entering the condenser level to assure that and condensate form in the condenser box does not return to the exhaust tube.

The use of a condenser box is advised when using a plastic tube as exhaust tube and may be redundant if using a metallic tube for exhaust as it is more likely that all exhaust moisture will condense in the exhaust tube attached to the cylindrical metal block because of the high conductivity of the metallic tube compared to the plastic tube.

Another alternate is to connect the bioreactor directly to the condenser box producing condensation in the condenser box that will not be returned to the bioreactor.

Figure 2:
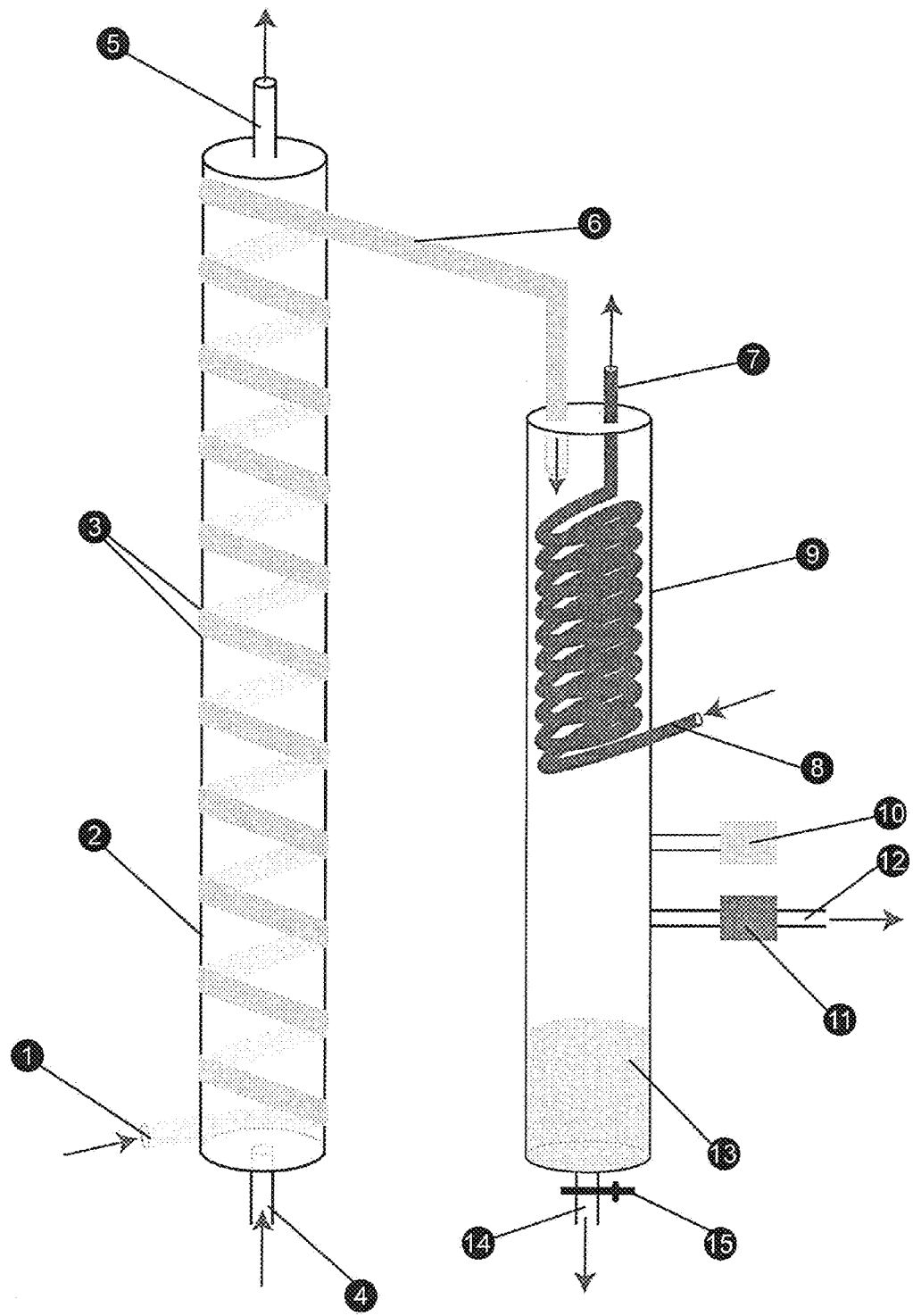
FIG. 2 is a lateral view of a bioreactor exhaust assembly with condenser.
Figure 3:
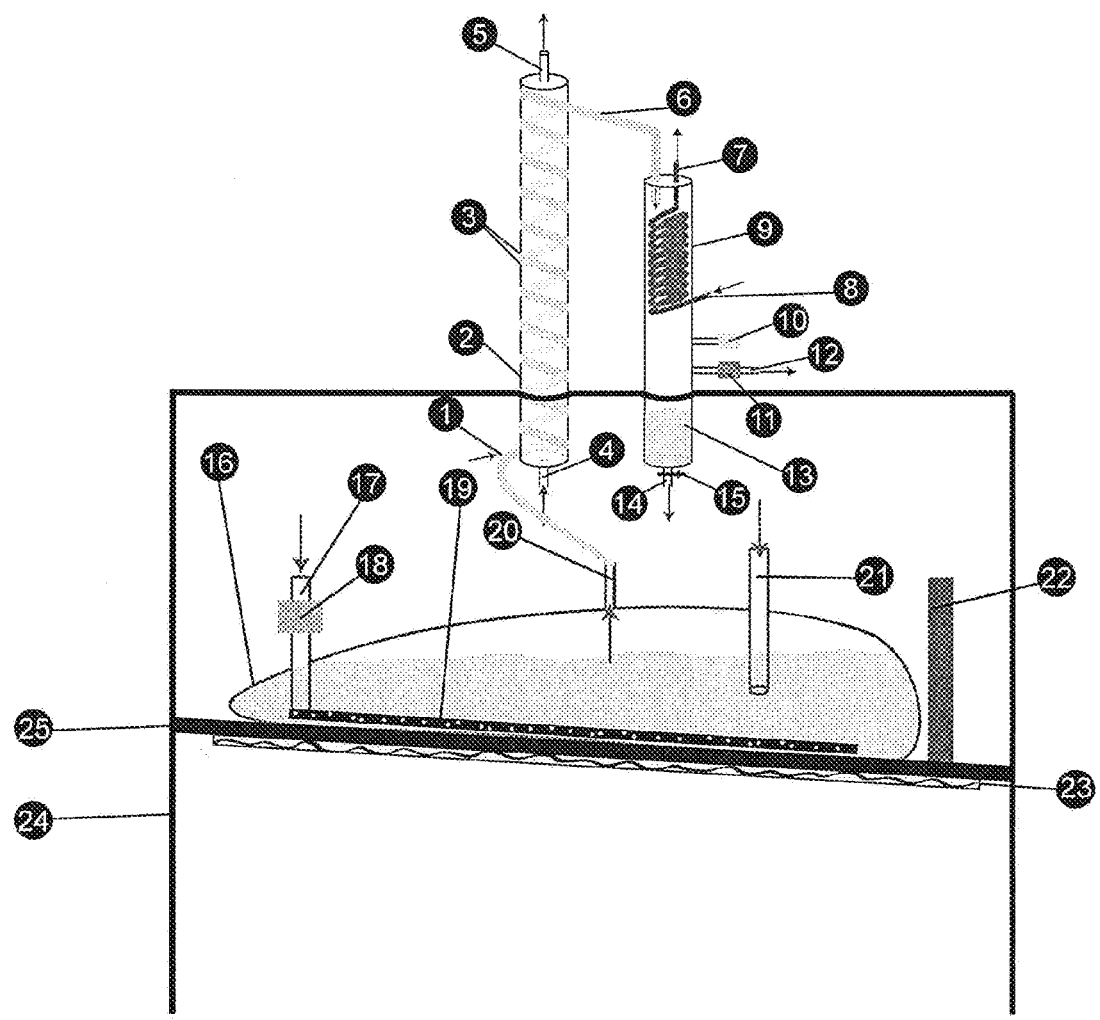
FIG. 3 is a lateral view of a bioreactor exhaust assembly with condenser and connected to a disposable bioreactor.

The preferred embodiments of the invention are shown in FIGS. 1-3.

FIG. 1 depicts a bioreactor exhaust assembly connected to a disposable bioreactor where 1: Flexible bioreactor bag; 2: gas inlet; 3: gas sterilizing filter; 4: Sparging filter; 5: Gas outlet; 6: Media inlet/outlet; 7: Flapper, 8: Resistive electrical heating element; 9: Vertical support legs; 10: Metal plate; 11: Flexible disposable exhaust tube; 12: Grooved metal block; 13: Liquid coolant in; 14: Liquid coolant out; 15: low-pressure relief valve; 16: exhaust to atmosphere; 17: Pressure meter.

The instant invention disclosed in FIG. 1 is operated by connecting the bioreactor exhaust assembly to a bioreactor gas port through a exhaust tube, which is kept cold by winding it on a grooved metal block, which is in turn kept cold by recirculation of cold liquids in it. The temperature of the exhaust tube is kept as close to 5-8 C as possible, well below the dew point of the gases inside the exhaust tube. As gases condense in the exhaust tube, the temperature inside the tube rises and as long as it remains above the dew point, the process would work efficiently. The condensate drips along the wall of the exhaust tube back to the bioreactor.

The specific shape of the path for the exhaust tube disclosed in the instant invention is critical to assuring that the condensate flows down along the wall of the exhaust tube despite the fast flow of gases in the tube. The condensate is essentially flowing against the path of fluidic gases that would keep it from flowing down if the diameter of the tube is too small and if the path of the tube is such that the condensate may form pockets along the wall of the tube. Since the aim of the invention is to vent out large volumes of gases, it is anticipated that the diameter of the tube would be large, such as greater than at least one-half inch in diameter. The remaining exhaust is then vented out when the pressure inside the tube rises above 0.05 inch water gauge using a low-pressure release valve.

It is important that the valve be of such type that once closed, it would provide a hermetic seal. This is a significant part of instant invention and mandates that only certain type of valves be used; valves that are based on the weight of the closing valve or those that are operated by the outgoing exhaust would be inadequate. One type of valve, though the choice is not limiting is a solenoid valve that closes once the pressure goes below the range specified; the action of the valve must also be instantaneous so that in the event of a fast pressure drop, the exhaust tube can be sealed instantly.

This embodiment represents a most common utility of the invention where the escaping gases are condensed in a vertical tube that is kept cold by winding it around a cold metal block; the grooves in the metal block allow maximum contact with the tube surface and thus maximizing heat transfer to the metal block. While this invention would prove useful for all types of materials used to construct the exhaust tube, using a metallic tube would significantly enhance the efficiency of the extraction of moisture from the exhaust.

The pressure sensor attached to the tube can be connected directly to the low-pressure relief valve to operate it automatically once a pre-determined pressure is reached in the exhaust tube.

The disclosed limits for closing and opening the valve are based on common understanding of the spatial design needed for isolating areas in a typical clean room. A pressure of 0.05 inch water gauge is sufficient to assure that there is no cross contamination from the low pressure area to the high pressure area; in this case the exhaust tube is a high pressure area. While a higher-pressure differential is always desirable, the advantages gained in raising the difference are minimal. On those situations where the pressure drops in the tube as a result of the wave motion in the flexible bag that might create a temporary depression in the bag of where the gas supply is interrupted in the bag, the valve will trigger to close the tube to make sure that no contaminants enter the bioreactor bag.

The current art recommends using sterilizing filters to prevent contamination from or to the biorectors. While this does represent a foolproof choice, it cannot be used in a flexible disposable bioreactor since the breakthrough pressure for these filters is very high (Table 1). As a comparison, the lowest pressure needed by these filters is about 3 psi or about 83 inches in a water gauge, this compares with 0.05 inches water gauge as disclosed in the instant invention. The pressure in the bag will build too high and might rupture the bag when high volumes of gases are exhausted such as at 1 vvm. It is noteworthy that most of the flexible bags used in bioreactors are capable of holding about 0.1 bar (about 40 inch water gauge) that can be easily exceeded when very high rates of flow through is anticipated and a filter is blocking the flow.

The features of the embodiments described above obviate at all of the problems in the current art, a loss of volume, a restriction in flow and prevention of cross contamination.

FIG. 2 describes a bioreactor exhaust that has two stages of condensation. (1) flexible disposable exhaust tube; (2) grooved metal block; (3) grooves; (4) liquid coolant in; (5) liquid coolant out; (6) condenser connection; (7) liquid coolant out for the condensing coil; (8) liquid coolant in for the condensing coil; (9) condenser box; (10) pressure sensor (11) low-pressure relief valve; (12) exhaust to atmosphere; (13) condensate reservoir; (14) condensate drain; and (15) stopcock for condensate drain.

The above embodiment operates in two stages. First, a condensate is formed as above in the first embodiment (FIG. 1) and then the exhaust gases are entered into a condenser box wherein they strike a cold condenser coil that instantly condenses any remaining moisture in the air and in doing so coalesces any fine liquid particles. This embodiment will be of greater use when the exhaust tube is non-metallic wherein there is a chance of some moisture escaping out uncondensed. The second condensate is kept within the condenser box and drained out when it reaches a certain level, thus keeping all contents of the bioreactor away from the room. The same type of pressure monitor and release valve operates as shown in FIG. 1 is used to release the gases into environment keeping a higher pressure inside the condenser box to assure that no air from room enters the bioreactor through the exhaust assembly.

FIG. 3 discloses a working model of a bioreactor exhaust connected to a bioreactor. (1) Flexible disposable exhaust tube; (2) grooved metal block; (3) grooves; (4) liquid coolant in; (5) liquid coolant out; (6) condenser connection; (7) liquid coolant out for the condensing coil; (8) liquid coolant in for the condensing coil; (9) condenser box; (10) pressure sensor; (11) low-pressure relief valve; (12) exhaust to atmosphere; (13) condensate reservoir; (14) condensate drain; (15) stopcock for condensate drain; (16) flexible bioreactor bag; (17) gas inlet; (18) gas sterilizing filter; (19) sparging filter; (20) gas outlet; (21) media inlet/outlet; (22) flapper; (23) resistive electrical heating element; (24) vertical support legs; and (25) metal plate.

The bioreactor of the instant invention above comprises a flexible disposable bag with an inlet for gas including a sterilizing filter and connectivity to a sparging tube disposed in the bag. The bioreactor bag also includes a gas outlet, which is attached to the instant invention, the exhaust assembly, and a nutrient media inlet and outlet. The bioreactor bag is placed on a stationary surface that has means of heating and a a flapper at one end to push down upon the bag to create wave motion inside the bag. While specific components and design elements are disclosed for the bioreactor, these may be changed as the bioreactor is merely an example of a source of exhaust gases.

The bioreactor is operated by first cooling down the exhaust tube and the condenser, introducing nutrient media in the bioreactor bag and biological culture and the bag allowed to heat to a desired temperature. The gassing is started and gases entering the exhaust tube are condensed to drain the condensate back into bioreactor bag. The exhaust then enters the condenser box wherein any remaining moisture and liquid is removed and the gases exhausted when the pressure inside the condenser bag rises above 0.05-inch water gauge. It is anticipated that in most instances the exhaust will remain open, as fast flowing gas would provide a pressure higher than 0.05-inch water gauge. Should the pressure drop due to the movement of fluid inside the bioreactor bag or to malfunction in the gassing of the bioreactor bag, the valve will close instantly to prevent contaminants from entering the bioreactor exhaust assembly and thus the bioreactor bag.

The components of the exhaust assembly described herein which come into contact with the culture medium or products provided thereby desirably comprise biocompatible materials, more desirably biocompatible polymers, and are preferably sterilizable.

It should also be understood that many of the components described herein also are desirably flexible, e.g., the containers desirably comprise flexible biocompatible polymer containers (such as collapsible bags), with the conduits also desirably comprising such biocompatible polymers. The flexible material is further desirably one that is USP Class VI certified, e.g., silicone, polycarbonate, polyethylene, and polypropylene. Non-limiting examples of flexible materials include polymers such as polyethylene (e.g., linear low density polyethylene and ultra low density polyethylene), polypropylene, polyvinylchloride, polyvinyldichloride, polyvinylidene chloride, ethylene vinyl acetate, polycarbonate, polymethacrylate, polyvinyl alcohol, nylon, silicone rubber, other synthetic rubbers and/or plastics. If desired, portions of the flexible container may comprise a substantially rigid material such as a rigid polymer (e.g., high density polyethylene), metal, and/or glass.

The components described herein that are metallic and come in contact with condensate that is returned to the bioreactor needs to be sterilizable as well. The preferred form for sterilizing these components would be to do in situ gamma sterilization where possible. Alternately, the metallic components can be sterilized separately and connected to the bioreactor under aseptic conditions or using sterile connectors.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of ventilating a bioreactor comprising:
   a. providing a bioreactor capable of holding cell culture and culture medium and growing the cell culture:
   b. providing a bioreactor exhaust assembly comprising:
      i. an exhaust tube with an inner volume having a lower end and an upper end, wherein the upper end is connected to a low pressure relief valve and a plurality of sensors including at least a pressure sensor;
      ii. wherein the exhaust tube is attached to a vertical surface capable of being cooled and held at a higher elevation than the lower end;
   c. attaching the lower end of the bioreactor exhaust assembly to a bioreactor;
   d. operating the bioreactor to grow a cell culture;
   e. cooling the vertical surface to maintain a temperature in the exhaust tube below the dew point of a gas in the exhaust tube;
   f. allowing the exhaust from the bioreactor to enter the exhaust tube;
   g. measuring the pressure in the exhaust tube using the pressure sensor;
   h. releasing the exhaust gas to atmosphere by opening the low pressure relief valve when the pressure in the exhaust assembly reaches a pressure above 0.05-inch (±10%) water gauge;
   i. closing the low pressure relief valve and stopping the exhaust of gas to atmosphere when the pressure inside the exhaust assembly reaches below 0.05-inch (±10%) water gauge; and
   j. repeating steps (f)-(h) till the end of the bioreaction cycle.

2. The method of claim 1, wherein the temperature in step (d) is between 5° C. and 8° C.

3. The method of claim 1, wherein the vertical surface comprises a condenser block comprising a recirculating cooling liquid.

4. The method of claim 3, wherein the cooling liquid causes a condensate to form in the exhaust assembly tube and then the condensate that forms flows back into the bioreactor.

5. The method of claim 1, wherein the exhaust assembly tube is at least one-half inch in diameter.

6. The method according to claim 1, wherein the exhaust assembly tube is flexible.

7. The method of claim 3, wherein the condenser block further comprises a temperature sensor to measure the temperature of the condenser.

8. A method of ventilating a bioreactor comprising:
   a. providing a bioreactor capable of holding cell culture and culture medium and growing the cell culture;
   b. providing a bioreactor exhaust assembly comprising:
      i. A bioreactor exhaust assembly comprising an exhaust tube with an inner volume and a lower end connected to a bioreactor and an upper end connected to a condenser, wherein the exhaust tube is held upright;
      ii. a vertical cylindrical block for wrapping the exhaust tube comprising a liquid inlet and a liquid outlet, wherein the exhaust tube is optionally held in place on the surface of the cylindrical block by a groove in the cylindrical block's surface;
      iii. wherein the condenser comprises a top and a bottom and an inner volume, a condenser coil, an inlet for liquid to cool the condenser coil, an outlet for recirculating the liquid in the condenser coil, a pressure sensor, a low pressure relief valve, an exhaust outlet, a plurality of sensors with at least a pressure sensor and a temperature sensor, a bottom drain and a stopcock to operate the drain;
   c. connecting the bioreactor exhaust assembly to a bioreactor;
   d. operating the bioreactor to grow a cell culture;
   e. passing liquid through the vertical cylindrical block to cool the exhaust gas;
   f. passing liquid through the condenser coil of the condenser;
   g. allowing the exhaust gas to pass through the exhaust tube into the condenser and collecting any condensate that forms;
   h. opening the low pressure release valve if the pressure rises above 0.05-inch (±10%) water gauge;
   i. closing the low pressure relief valve and stopping the exhaust of gas to atmosphere when the pressure inside the exhaust assembly reaches below 0.05-inch (±10%) water gauge;
   j. opening the stopcock in the bottom drain of the condenser to remove condensate;
   k. repeating steps (f)-(i) till the end of the bioreaction cycle.

9. The method of claim 8, wherein the condenser block further comprises a temperature sensor to measure the temperature of the condenser.

10. The method of claim 9, wherein the temperature of the vertical cylindrical block and the condenser coil is maintained between 5° C. and 8° C.

* * * * *